US006538103B1

(12) United States Patent
Ji et al.

(10) Patent No.: US 6,538,103 B1
(45) Date of Patent: Mar. 25, 2003

(54) LYSINE BINDING FRAGMENTS OF ANGIOSTATIN

(75) Inventors: Richard Wei-Dong Ji, Lawrenceville, NJ (US); Pamela A. Trail, Yardley, PA (US)

(73) Assignee: Bristol--Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/348,953

(22) Filed: Jul. 7, 1999

Related U.S. Application Data

(60) Provisional application No. 60/092,831, filed on Jul. 14, 1998.

(51) Int. Cl.[7] .................................................. C07K 5/00
(52) U.S. Cl. ........................................... 530/300; 514/2
(58) Field of Search ..................... 435/69.1; 424/94.64; 530/300; 514/2

(56) References Cited

U.S. PATENT DOCUMENTS

| | | | |
|---|---|---|---|
| 5,639,725 A | 6/1997 | Protein | 435/69.1 |
| 5,733,876 A | 3/1998 | O'Reilly et al. | |
| 5,945,403 A | 8/1999 | Folkman et al. | |
| 5,981,568 A | 11/1999 | Kunz et al. | |

FOREIGN PATENT DOCUMENTS

| | | |
|---|---|---|
| WO | WO 97/41824 | 11/1997 |
| WO | WO 99/35248 | 7/1999 |

OTHER PUBLICATIONS

Cao, Y. et al., The Journal of Biological Chemistry, vol. 272, No. 36, pp. 22924–22928 (1997).
Cao et al. Kringle domains of human angiostatin. J Biol Chem., vol. 271(15): 29461–29467, 1996.*
Cao Yiahai et al., Kringle domains of human angiostatin—charecterization of the anti-proliferative activity on endothelial cells. J Biol Chem, 271(46); 29461–29467, 1996.*
Ji, Weidong–Richard et al., FASEB Journal, vol. 12, No. 15, Dec. 1998, pp. 1731–1738.
Ji, Weidong–Richard et al., Biochem. Biophys. Res. Commun 247, May 1998, pp. 414–419.
Dvorak et al. (1991) "Distribution of Vascular Permeability Factor (Vascular Endothelial Growth Factor) in Tumors: Concentration in Tumor Blood Vessels" J. Exp. Med. 174, 1275–1278.
Gross et al. (1993) "Effects of Modulation of Basic Fibroblast Growth Factor on Tumor Growth in Vivo" J. Natl. Cancer Inst. 85(2), 121–131.
Kim et al. (1993) "Inhibition of vascular endothelial growth factor–induced angiogenesis suppresses tumour growth in vivo" Nature 362(6243), 841–844.
Lin et al. (1997) "Inhibition of Tumor Angiogenesis Using a Soluble Receptor Establishes a Role for Tie2 in Pathologic Vascular Growth" J. Clin. Invest. 100(8), 2072–2078.

Millauer et al. (1994) "Glioblastoma growth inhibited in vivo by a dominant–negative Flk–1 mutant" Nature 367(6463), 576–579.
O'Reilly et al. (1994) "Angiostatin: A Novel Angiogenesis Inhibitor that Mediates the Supression of Metastases by a Lewis Lung Carcinoma" Cell 79, 315–328.
O'Reilly et al. (1997) "Endostatin: An Endogenous Inhibitor of Angiogenesis and Tumor Growth" Cell 88(2), 277–285.
Brooks et al. (1995) "Antiintegrin αv β blocks human breast cancer growth angiogenesis in human skin" J. Clin. Invest. 96(4), 1815–1822.
Ingber et al. (1990) "Synthetic analogues of fumagillin that inhibit angiogenesis and suppress tumour growth" Nature 348, 555–557.
Ezekowitz et al. (1992) "Interferon Alfa–2a Therapy for Life–Threatening Hemangiomas of Infancy" New Engl. J. Med. 326, 1456–1463.
Wiman et al. (1978) "5'–AMP is a direct precursor of cytokinin in Dictyostelium discoideum" Nature 272, 545–549.
Dong et al. (1997) "Macrophage–derived metalloelastase is responsible for the generation of angiostatin in Lewis Lung carcinoma"'Cell 88(6), 801–810.
Patterson et al. (1997) "Angiostatin–converting Enzyme Activities of Human Matrilysin (MMP-7) and Gelatinase B/Type IV Collagenase (MMP-9)" J. Biol. Chem. 272(46), 28823–28825.
O'Reilly et al. (1996) "Anagiostatin induces and sustains dormancy of human primary tumors in mice" Nat. Med. 2(6), 689–692.
Lannutti et al. (1997) "Human Angiostatin inhibits Murine Hemangioendothelioma Tumor Growth in Vivo" Cancer Res. 57(7) 1329–1334.
Wu et al. (1997) "Suppression of Tumor Growth with Recombinant Murine Angiostatin" Biochem.Biophys.Res. Commun. 236, 651–654.
Sim et al. (1997) "A Recombinant Human Angiostatin Protein inhibits Experimental Primary and Metastatic Cancer" Cancer Res. 57(7) 1329–1334.
Gately et al. (1997) "The mechanism of cancer–mediated conversion of plasminogen to the angiogenesis inhibitor angiostatin" Proc. Natl. Acad. Sci. USA 97(20) 10868–10872.
Cao et al. (1996) "Kringle Domains of Human Angiostatin" J. Biol. Chem. 271, 29461–29467.

(List continued on next page.)

Primary Examiner—Jeffrey Fredman
Assistant Examiner—Suryaprabha Chunduru
(74) Attorney, Agent, or Firm—Keith R. Lange; Audrey F. Sher (57) ABSTRACT

The present invention concerns peptide fragments of angiostatin containing lysine-binding sites of angiostatin which can be used as anti-angiogenic agents for the treatment of cancer, diabetic retinopathy, rheumatoid arthritis, psoriasis, atherosclerotic plaque formation, and any disease process that involves angiogenesis. The lysine binding fragments are derived from kringles 1,2 and/or 4 of plasminogen.

2 Claims, 4 Drawing Sheets

OTHER PUBLICATIONS

Folkman (1995) "Angiogenesis in cancer, vascular, rheumatoid and other disease" Nat. Med. 1, 27–31.

Folkman (1995) "Clinical Applications of Research of Angiogenesis" New Engl. J. Med. 285, 1757–1763.

Folkman (1971) "Tumor Angiogenesis: Therapeutic Implications" New Engl. J. Med. 285, 1182–1186.

Folkman et al. (1992) "Angiogenesis" J. Biol. Chem. 267, 10931–10934.

Shing et al. (1984) "Heparin Affinity: Purification of a Tumor–Derived Capillary Endothelial Cell Growth Factor" Science 223, 1296–1298.

Maciag et al. (1984) "Heparin Binds Endothelial Cell Growth Factor, the Principal Endothelial Cell Mitogen in Bovine Brain" Science 225, 932–935.

Ferrara et al. (1989) "Pituitary Follicular Cell Secrete a Novel Heparin–Binding Growth Factor Specific for Vascular Endothelial Cells" Biochem. Biophys. Res. Commun. 161, 851–855.

Nguyen et al. (1994) "Elevated Levels of an Angiogenic Peptide, Basic Fibroblast Growth Factor, in the Urine of Patients with a Wide Spectrum of Cancers" J. Natl. Cancer Inst. 86, 356–361.

* cited by examiner

LYSINE BINDING FRAGMENTS OF ANGIOSTATIN

CROSS REFERENCE TO RELATED APPLICATION

This application claims priority from provisional U.S. application Ser. No. 60/092,831, filed Jul. 14, 1998, incorporated herein by reference in its entirety.

FIELD OF THE INVENTION

The present invention concerns peptide fragments of angiostatin containing lysine-binding sites of angiostatin, including small molecules that mimick their functions, which can be used as anti-angiogenic agents for the treatment of cancer, diabetic retinopathy, rheumatoid arthritis, psoriasis, atherosclerotic plaque formation, and any disease process that involves angiogenesis.

BACKGROUND OF THE INVENTION

Different than de novo vascularization, angiogenesis is the process of neovascularization from pre-existing blood vessels. It has pronounced effects in a wide array of physiological conditions, such as placenta development and embryogenesis. An imbalance of the angiogenic process has been shown to contribute to pathological disorders such as diabetic retinopathy, rheumatoid arthritis, and psoriasis (Folkman, J. (1995) Nat. Med. 1, 27–31; Folkman, J. (1995) New Engl. J. Med. 333, 1757–1763). Particularly, both primary and metastatic tumors need to recruit neovessels for their growth expansion (Folkman, J. (1971) New Engl. J. Med. 285, 1182–1186; Folkman, J., and Shing, Y. (1992) J. Biol. Chem. 267, 10931–10934).

There is a mounting body of evidence supporting the concept that angiogenesis is a prerequisite for tumor growth. Such a correlation has been established by blocking positive regulators of angiogenesis or utilizing negative regulators to suppress angiogenesis that resulted in a delay or regression of experimental tumors. Vascular endothelial growth factor (VEGF) and fibroblast growth factor (FGF) are potent mitogens and strong chemoattractants for endothelial cells (Shing Y., Folkman J., Sullivan, R., Butterfield, C., Murray, J., Klagsbrun, M. (1984) Science 223, 1296–1298; Maciag, T., Mehlnan, T., Friesel, R., and Schreiber, A. (1984) Science 225, 932–935; Ferrara, N. and Henzel, W. J. (1989) Biochem. Biophys. Res. Commun. 161, 851–855). Their roles in inducing tumor angiogenesis have been demonstrated in a variety of human tumors (Nguyen, M., Watanabe, H., Budson, A. E., Richie, J. P., Hayes, D. F., and Folkman, J. (1994) J. Natl. Cancer Inst. 86, 356–361; Dvorak, H. F., Sioussat, T. M., Brown, L. F., Berse, B., Nagy, J. A., Sotrel, A., Manseau, E. J., Van de Water, L., and Senger, D. R. (1991) J. Exp. Med. 174, 1275–1278). Antibodies neutralizing VEGF or FGF caused a marked decrease of tumor growth via angiogenic inhibition (Gross, J. L., Herblin, W. F., Dusak, B. A., Czerniak, P., Diamond, M. D., Sun, T., Eidsvoog, K., Dexter, D. L., and Yayon, A. (1993) J. Natl. Cancer Inst. 85(2), 121–131; Kim, K. J., Li, B., Winer, J., Armanini, M., Gillett, N., Phillips, H. S., and Ferrara, N. (1993) Nature 362(6243), 841–844). Such anti-angiogenic and anti-tumor effects were also observed by antagonizing the corresponding receptors for these endothelial cell mitogens. A soluble form of Tie-2 receptor, a receptor tyrosine kinase preferentially expressed on vascular endothelium, exhibited effective inhibition of tumor angiogenesis (Lin, P., Polverini, P., Dewhirst, M., Shan, S., Rao, P. S., and Peters, K. (1997) J. Clin. Invest. 100(8), 2072–2078). Similarly, a dominant negative mutant of the VEGF receptor, Flk-1, prevented VEGF-induced angiogenesis by dimerizing and deactivating the endogenous Flk-1 (Millauer, B., Shawver, L. K., Plate, K. H., Risau, W., and Ullrich, A. (1994) Nature 367(6463), 576–579). In addition, negative regulators of angiogenesis, such as angiostatin, endostatin, and antagonists for integrin $\alpha v\beta 3$, displayed profound anti-tumor activities in vivo (O'Reilly, M. S., Holmgren, L., Shing, Y., Chen, C., Rosenthal, R. A., Moses, M., Lane, W. S., Cao, Y., Sage, E. H., and Folkman, J. (1994) Cell 79, 315–328; O'Reilly, M. S., Boehm, T., Shing, Y., Fukai, N., Vasios, G., Lane, W. S., Flynn, E., Birkhead, J. R., Olsen, B. R., and Folkman, J. (1997) Cell 88(2), 277–285; Brooks, P. C., Stromblad, S., Klemke, R., Visscher, D., Sarkar, F. H., and Cheresh, D. A. 1995) J. Clin Invest. 96(4), 1815–1822). TNP-470 and Interferon alfa-2a also manifested clinical evidence that tumor growth could be therapeutically intervened using an anti-angiogenic approach (Ingber, D., Fujita, T., Kishimoto, S., Sudo, K., Kanamaru, T., Brem, H., and Folkman, J. (1990) Nature 348, 555–557; Ezekowitz, R. A., Mulliken, J. B., and Folkman, J. (1992) N. Engl. J. Med. 326, 1456–1463).

Angiostatin was initially isolated from urine and sera of mice bearing Lewis Lung carcinoma (O'Reilly, M. S., et al., (1994) Cell; U.S. Pat. No. 5,639,725). It is an approximately 38–45kD internal fragment of plasminogen, which consists of 4 triple-disulfide bridged kringle structures. Both kringle 1 and 4 have lysine-binding sites, which are responsible for anchoring the plasminogen molecule on fibrin-rich blood clots (Wiman, B. and Collen, D. (1978) Nature 272, 549–545). Angiostatin was originally generated from plasminogen by proteolytic cleavage with porcine pancreatic elastase (O'Reilly, M. S., et al., (1994) Cell). Subsequent studies have shown that angiostatin can be generated from plasminogen by a variety of physiological and pathological proteases, including macrophage-derived metalloelastases (Dong, Z., Kumar, R., Yang, X., Fidler, I. J. (1997) Cell 88(6), 801–810), members of matrix metalloproteinase (MMP) family, such as matrilysin (MMP-7) or gelatinase B/type IV collagenase (MMP-9) (Patterson, B. C. and Sang, Q. A. (1997) J. Biol. Chem. 272(46), 28823–28825), and Urokinase (Gately, S., Twardowski, P., Stack, M. S., Cundiff, D. L., Grella, D., Castellino, F. J., Enghild, J., Kwaan, H. C., Lee, F., Kramer, R. A., Volpert, O., Bouck, N., and Soff, G. A. (1997) Proc. Natl Acad. Sci. USA 94(20), 10868–10872). Angiostatin was found to inhibit endothelial cell proliferation in vitro and block growth factor, such as basic FGF, elicited angiogenesis in vivo. Elastase-cleaved angiostatin was shown to induce dormancy of several metastatic and primary tumors, including carcinomas of breast, prostate, colon, and lung (O'Reilly, M. S., et al., (1994) Cell; O'Reilly, M. S., Holmgren, L., Chen, C., and Folkman, J. (1996) Nat. Med. 2(6), 689–692). Angiostatin generated by urokinase cleavage significantly reduced the growth of a murine hemangioendothelioma in vivo (Lannutti, B. J., Gately, S. T., Quevedo, M. E., Soff, G. A., and Paller, A. S. (1997) Cancer Res. 57, 5277–5280). Recombinant angiostatin also produced anti-tumor effects in vivo via the blocking of tumor angiogenesis (Wu, Z., O'Reilly, M. S., Folkman, J., and Shing, Y. (1997) Biochem. Biophys. Res. Commun. 236, 651–654; Sim, B. K., O'Reilly, M. S., Liang, H., Fortier, A. H., He, W., Madsen, J. W., Lapcevich, R., and Nacy, C. A. (1997) Cancer Res 57(7), 1329–1334). These anti-tumor effects were accompanied by a marked reduction of microvessel density within the tumor mass, indicating that suppression of angiogenesis led to the inhibition of tumor growth.

Angiogenesis is a complex process that entails an orchestration of endothelial cell proliferation, migration, basement membrane degradation, and neovessel assembly. The kringle domains of angiostatin were shown to exhibit divergent inhibitory activities for endothelial cell proliferation (Cao, Y., Ji, R. W., Davidson, D., Schaller, J., Marti, D., Sohndel, S., McCance, S. G., O'Reilly, M. S., Llinas, M., and Folkman, J. (1996) *J. Biol. Chem.* 271, 29461–29467). Kringle 1–3 manifested a potent inhibition of endothelial cell proliferation whereas kringle 4 had only marginal effect. Kringle conformation was also shown to be essential for the potent anti-proliferative activity of angiostatin.

SUMMARY OF THE INVENTION

Angiostatin (approximately kringle regions 1–4 ("K1-4") of human plasminogen) has been described as a potent angiogenesis inhibitor. We now demonstrate that the blocking of the lysine-binding sites of angiostatin (K1-4) completely abolishs its inhibitory activities of endothelial cell migration, a process crucial for angiogenesis. The present invention is directed to a fragment of kringle 1 of human plasminogen or variant thereof containing a lysine binding site and having anti-angiogenic activity. The present invention is also directed to a fragment of kringle 2 of human plasminogen or variant thereof containing a lysine binding site and having anti-angiogenic activity. The present invention is further directed to a fragment of kringle 4 of human plasminogen or variant thereof containing a lysine binding site and having anti-angiogenic activity.

DETAILED DESCRIPTION OF THE INVENTION

Figure 1:
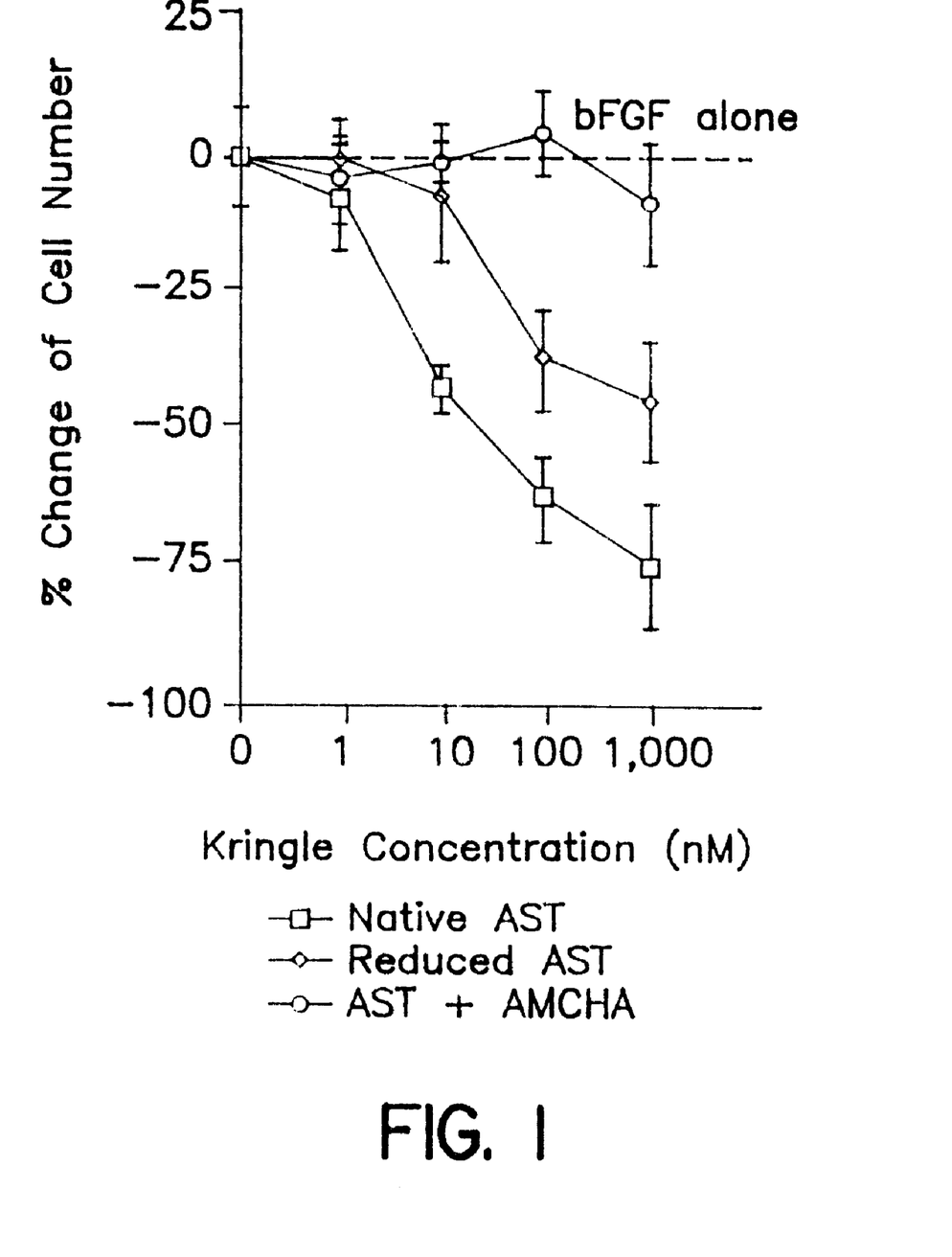
FIG. 1. Kringle structure and lysine-binding sites are essential for the anti-migratory activities of angiostatin. Inhibition of endothelial cell migration by native angiostatin, reduced/alkylated angiostatin, and the AMCHA-blocked angiostatin. AMCHA, a high affinity lysine analogue, was used to block the lysine-binding sites of angiostatin. The dashed lines indicate the baseline migration of endothelial cells in the presence of bFGF. Each data point represents the mean of three determinations (with standard error) as a percentage of inhibition.
Figure 2:
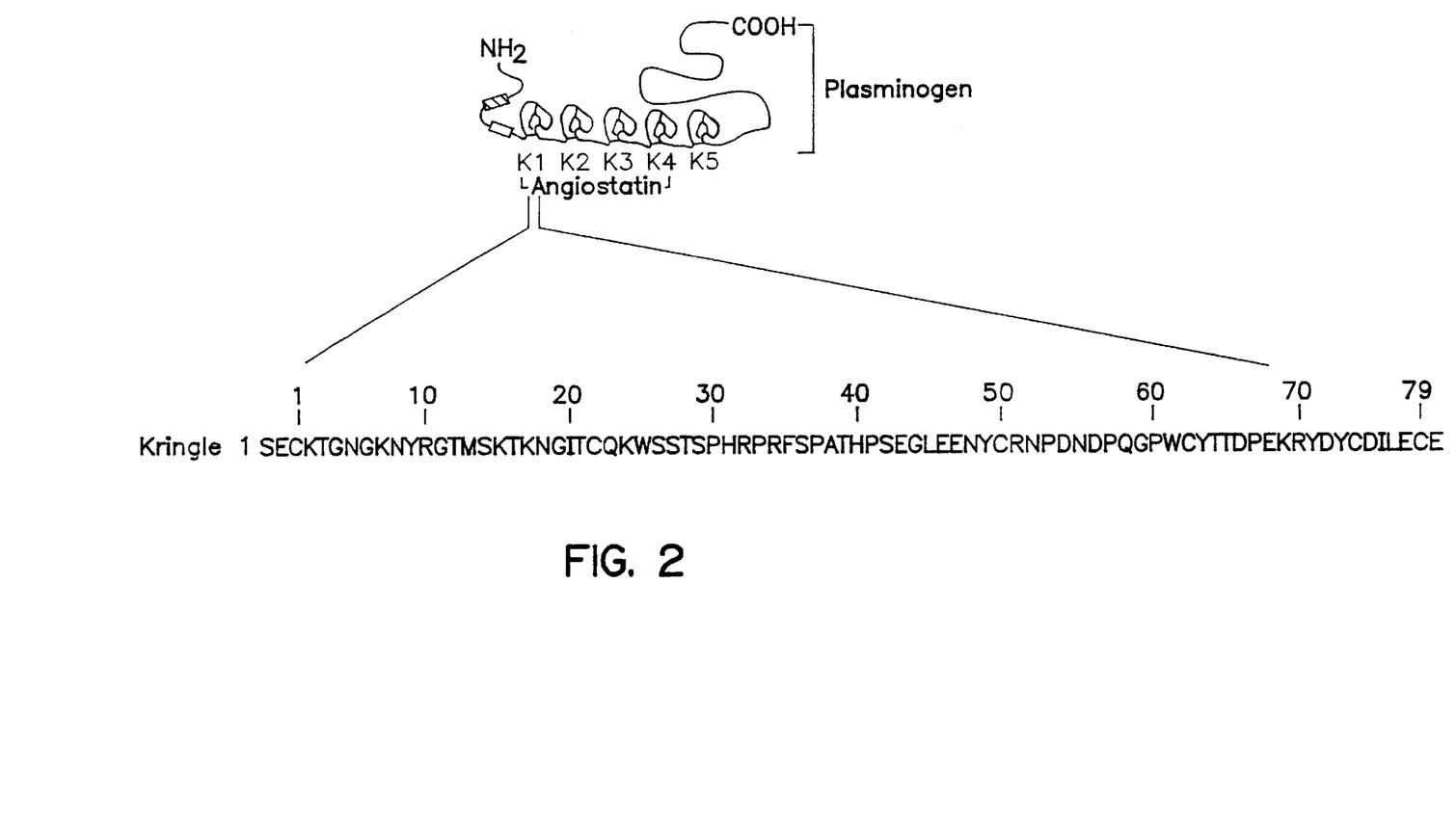
FIG. 2. Schematic representation of human plasminogen showing the amino acid sequence of kringle 1 (SEQ ID NO.1) and the numbering system used herein for the amino acid positions of kringle 1.
Figure 3:
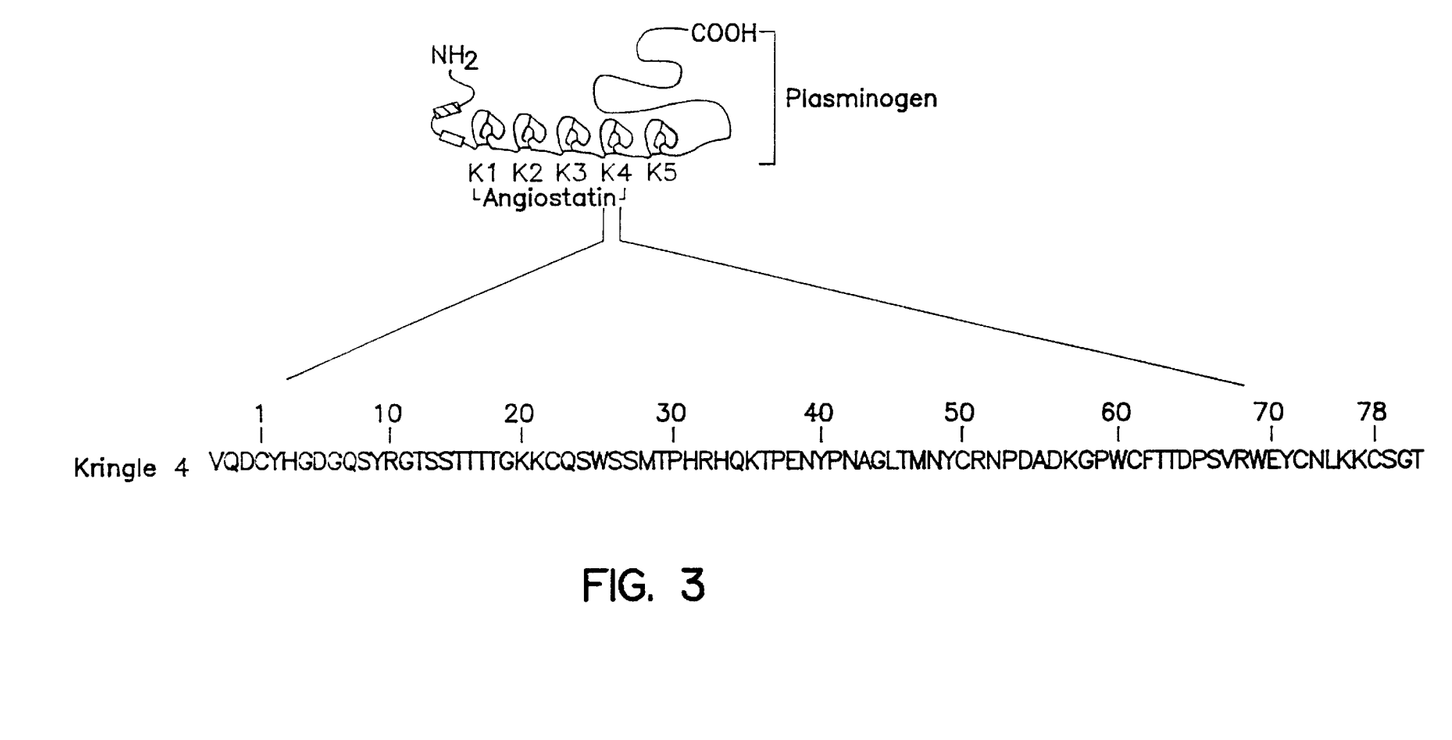
FIG. 3. Schematic representation of human plasminogen showing the amino acid sequence of kringle 4 (SEQ ID NO.2) and the numbering system used herein for the amino acid positions of kringle 4.
Figure 4:
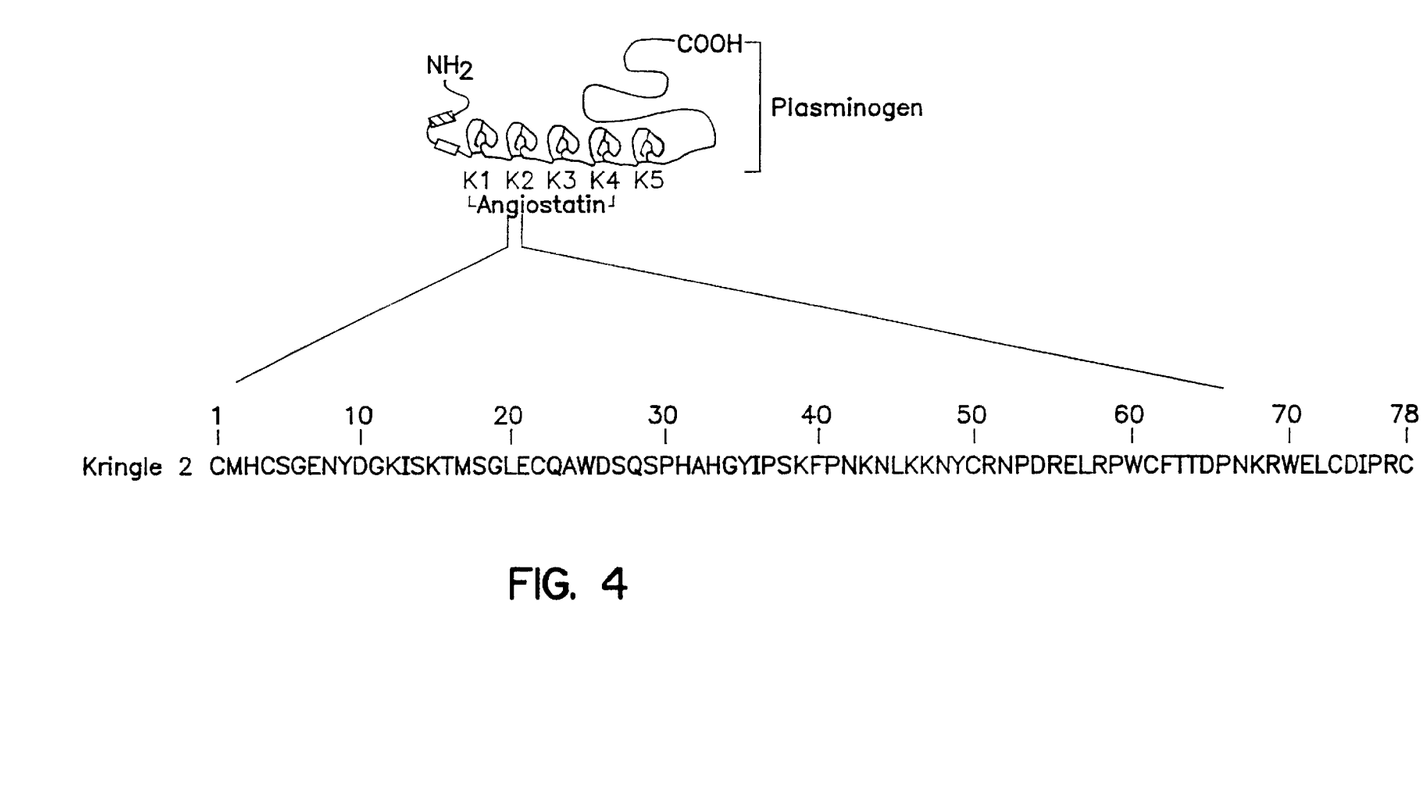
FIG. 4. Schematic representation of human plasminogen showing the amino acid sequence of kringle 2 (SEQ ID NO.3) and the numbering system used herein for the amino acid positions of kringle 2.

Abbreviations used herein as as follows: FGF, fibroblast growth factor; VEGF: vascular endothelial growth factor; bFGF, basic fibroblast growth factor; BCE, bovine capillary endothelial cell; DMEM, Dulbecco's modified Eagle's medium; AMCHA, trans-aminomethylcyclohexanecarboxylic acid; PCR, polymerase chain reaction; HPg, human plasminogen; PAGE: polyacrylamide gel electrophoresis; K1: plasminogen kringle region 1; K2: plasminogen kringle region 2; K3: plasminogen kringle region 3; K4: plasminogen kringle region 4. When a particular amino acid is immediately followed by a number, this represents the amino acid at the identified position on the appropriate kringle region using the numbering systems shown in FIGS. 2 and 3; for example, Trp60 of kringle 4 refers to tryptophan at position 60 as shown in FIG. 3.

All DNA sequences are represented herein by formulas whose left to right orientation is in the conventional direction of 5' to 3'. Nucleotide base abbreviations used herein are conventional in the art, i.e., T is thymine, A is adenine, C is cytosine, and G is guanine.

All amino acid residues identified herein are in the natural L-configuration. In keeping with standard polypeptide nomenclature, J. Biol. Chem. 243, 3557–3559 (1969), abbreviations for amino acid residues are as shown in the following Table of Correspondence:

| TABLE OF CORRESPONDENCE | | |
|---|---|---|
| SYMBOL | | |
| 1-Letter | 3-Letter | AMINO ACID |
| Y | Tyr | L-tyrosine |
| G | Gly | L-glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine |

All amino acid sequences are represented herein by formulas whose left to right orientation is in the conventional direction of amino-terminus to carboxy-terminus.

Angiostatin has been described as a potent angiogenesis inhibitor that can markedly suppress the growth of a variety of tumors, including carcinomas of lung, prostate, colon, and breast. Angiostatin and the sequences of mouse, human, rhesus monkey, procine and bovine plasminogen are given in U.S. Pat. No. 5,639,725, the disclosure of which is incorporated herein by reference in its entirety. Among individual kringle fragments, the lysine-binding K 1 and K4 are the most efficacious inhibitors of endothelial cell proliferation and migration, respectively. It is demonstrated herein that the blocking of lysine-binding sites with AMCHA, a high affinity lysine analogue, abolishes the anti-migratory activity of angiostatin. Thus, it has been discovered that the lysine-binding sites of angiostatin including its smaller peptide fragments or small molecules that mimick its function, can be used as anti-angiogenic agents for the treatment of conditions such as cancer, diabetic retinopathy, rheumatoid arthritis, psoriasis, atherosclerotic plaque formation, and any process that involves angiogenesis.

The present invention concerns a fragment of kringle 1 of human plasminogen or variant thereof containing a lysine binding site and having anti-angiogenic activity. It is preferred the fragment of K1 contains less than 70 amino acids, preferably 9 to 70 amino acids, more preferably 15 to 50 amino acids, even more preferably 30 to 45 amino acids, and even more preferably 35 to 40 amino acids. It is further preferred that the K1 fragment has at least one of Asp54, Asp56, Arg34, Lys69, Arg70, Tyr63, Trp61, Tyr71 or any combination thereof. More preferably the fragment of K1 has all of Asp54, Asp56, Arg34, Arg,69, Arg70, Tyr63, Trp61, and Tyr71.

The present invention is also directed to a fragment of kringle 4 of human plasminogen or variant thereof containing a lysine binding site and having anti-angiogenic activity. Preferably the fragment of K4 contains less than 70 amino acids, more preferably 9 to 70 amino acids, even more preferably 15 to 50 amino acids, and even more preferably 15 to 25 amino acids, and even more preferably 15 to 20 amino acids. It is further preferred that the fragment of K4 has at least one of Asp56, Arg69, Trp60, Trp70, Asp 54, Tyr72 or any combination thereof. More preferably the fragment of K4 has all of Asp56, Arg69, Trp60, Trp70, Asp 54, and Tyr72.

The present invention is further directed to a fragment of kringle 2 of human plasminogen or variant thereof containing a lysine binding site and having anti-angiogenic activity. Preferably the fragment of K2 contains less than 70 amino acids, more preferably 9 to 70 amino acids, even more preferably 15 to 55 amino acids, and even more preferably 40 to 50 amino acids. It is further preferred that he fragment of K2 has at least one of Trp25, Tyr35, Asp54, Glu56, Trp60, Phe62, Trp70 or any combination thereof. More preferably the fragment of K4 has all of Trp25, Tyr35, Asp54, Glu56, Trp60, Phe62, and Trp70.

A preferred fragment of the invention is a fragment of K1 from Arg34 through Tyr71. This fragment has the following sequence (SEQ ID NO:4):
R F S P A T H P S E G L E E N Y C R N P D N D P Q G P W-CYTTDPEKRY.

Another preferred fragment of the invention is a fragment of K4 from Asp56 through Tyr72. This fragment has the following sequence (SEQ ID NO:5):
DKGPWCFTTDPSVRWEY.

Still another preferred fragment of the invention is a fragment of K2 from Trp25 through Trp70. This fragment has the following sequence (SEQ ID NO:6):
W D S Q S P H A H G Y I P S K F P N K N L K K N Y C R N-PDRELRPWCFTTDPNKRW.

The present invention also contemplates fusion proteins with the fragments of K1, K2 and/or K4 with at least a second peptide. For example, a fusion protein may be made to couple one or more active fragments together in order to increase potency. Also, such fusion proteins can be designed to aid in purification. A preferred fusion protien of the invention comprises one or more active fragments fused to an immunoglobulin Fc domain and/or a signal sequence. Preferred immunoglobulin Fc domains and signal sequences are disclosed in U.S. Pat. No. 5,541,087, the disclosure of which is incorporated herein by reference in its entirety.

It is also contemplated that the present invention encompasses variants of the active fragments that retain anti-angiogenic activity. As used in the present application, the term "variant", when referring to a sequence, means a sequence which differs from the wild-type sequence found in nature, but still retains anti-angiogenic activity. It will be understood that allelic variations of the nucleic acid and amino acid sequences useful herein naturally exist, or may be intentionally introduced using methods known in the art. These variations may be demonstrated by one or more amino acid differences in the overall sequence, or by deletions, substitutions, insertions, inversions or additions of one or more amino acids in said sequence. Such amino acid substitutions may be made, for example, on the basis of similarity in polarity, charge, solubility, hydrophobicity, hydrophilicity and/or the amphipathic nature of the residues involved. For example, negatively charged amino acids include aspartic acid and glutamic acid; positively charged amino acids include lysine and arginine; amino acids with uncharged polar head groups or nonpolar head groups having similar hydrophilicity values include the following: leucine, isoleucine, valine, glycine, alanine, asparagine, glutamine, serine, threonine, phenylalanine, tyrosine. Other contemplated variations include salts and esters of the aforementioned polypeptides, as well as precursors of the aforementioned polypeptides, for example, precursors having N-terminal substituents such as methionine, N-formylmethionine and leader sequences. All such variations are included within the scope of the present invention.

The polypeptides of the present invention may be obtained by synthetic means, i.e., chemical synthesis of the polypeptide from its component amino acids, by methods known to those of, ordinary skill in the art. For example, the solid phase procedure described in Houghton et al., Proc. Natl. Acad. Sci. 82, 5131–5135 (1985) may be employed. The polypeptides may be obtained by production in prokaryotic or eukaryotic host cells expressing a DNA sequence coding for all or part of the desired fragment, or by in vitro translation of the mRNA encoded by a DNA sequence coding for the desired peptide. For example, a DNA sequence encoding SEQ.ID.NOS.4,5 or 6 may be synthesized as described below and inserted into a suitable expression vector, which in turn may be used to transform a suitable host cell. The recombinant host cell may then be cultured to produce the desired peptide. Techniques for the production of polypeptides by these means are known in the art, and are described herein.

The polypeptides produced in this manner may then be isolated and purified to some degree using various protein purification techniques. For example, chromatographic procedures such as ion exchange chromatography, gel filtration chromatography and immunoaffinity chromatography may be employed.

If the polypeptides of the invention is made through recombinant techniques, the DNA sequences useful to prepare the polypeptides of the invention can be obtained using various methods well-known to those of ordinary skill in the art. The expression vectors can be partly or wholly synthesized chemically and/or partly or wholly prepared through genetic engineering techniques. Fragments can be sequentially ligated (via appropriate terminal restriction sites or complementary terminal sequences) so as to form the correct linear sequence of nucleotides.

Expression Vectors

Expression vehicles of the invention for production of the anti-angiogenic polypeptides of the invention include plasmids or other vectors. In general, such vectors contain control sequences that allow expression in various types of hosts. Suitable expression vectors containing the desired coding and control sequences may be constructed using standard recombinant DNA techniques known in the art, many of which are described in Sambrook et al. (1989), *Molecular Cloning: A Laboratory Manual, 2nd* edition, Cold Spring Harbor Laboratory, Cold Spring Harbor, N.Y.

An expression vector as contemplated by the present invention is capable of directing the replication of the vector in bacteria, yeast, insect, and/or mammalian cells. One class of vectors utilizes yeast DNA elements that provide autonomously replicating origins such as the yeast 2μ element or ARS1 sequence which yield extrachromosomal plasmids. A second class of vectors relies upon the integration of the desired gene sequences into the host cell chromosome. The vectors may also incorporate a bacterial origin of replication. Suitable bacterial origins of replication include, for example, the ColE1, pSC101 and M13 origins of replication.

Expression vectors useful of the present invention typically contain a promoter located 5' to (i.e., upstream of) the DNA sequence to be expressed, and a transcription termination sequence located 3' to (i.e., downstream of) the sequence to be expressed. Suitable promoters include, for example, the yeast ADH1 promoter. The promoter sequence may also be inducible, to allow modulation of expression (e.g., by the presence or absence of nutrients or other inducers in the growth medium). Examples include the yeast GAL1, CUP1, and MET25 promoters. Suitable termination sequences include, for example, the yeast CYC1 termination and polyadenylation sequences.

The expression vectors may also include other regulatory sequences for optimal expression of the desired product. Such sequences include secretory leader sequences, which provide for secretion of the expressed product or direct membrane localization, and restriction enzyme recognition sequences, which provide sites for cleavage by restriction endonucleases. All of these materials are known in the art and some are commercially available.

A suitable expression vector may also include marking sequences, which allow phenotypic detection and/or selection of transformed yeast or bacterial cells. Such a marker may provide prototrophy to an auxotrophic host (e.g., amino acid biosynthetic genes), biocide resistance or supersensitivity (e.g., antibiotic resistance) or a phenotypically detectable signal (e.g., fluorescence). The selectable marker gene can be either directly linked to the DNA gene sequences to be expressed, or introduced into the same cell by transformation. Examples of yeast selectable markers include *Basidium pullulans* AUR1-C gene, the *S. cerevisiae* URA3 or LEU2 genes and the like. Examples of bacterial selectable markers include the ampicillin resistance gene. A preferred vector is pYESII, containing the ColE1 and 2μ origins of replication, the yeast URA3 and bacterial $amp^R$ genes, and the yeast GAL1 promoter sequence (Invitrogen).

In a further alternative, the constructs may be introduced into a cell by transformation in conjunction with a gene allowing for selection where the construct will become integrated into the host genome or persist episomally. Usually, the construct will be part of a vector having homologous sequences for integration or a replication system recognized by the host cell.

Host Cells

The present invention additionally concerns hosts for the expression of the above-noted expression vectors. Suitable host cells are yeasts. Examples include Saccharomyces species (e.g., *S. cerevisiae*), Candida species (e.g., *C. albicans*), and Schizosaccharomyces species (e.g., *S. pombe*) in which endogenous activities do not interfere with the function of the protein under study.

Expression vectors may be introduced into host cells by various methods known in the art. For example, transformation of host cells with expression vectors can be carried out by the alkali cation method. However, other methods for introducing expression vectors into host cells, for example, electroporation and spheroplast transformation can also be employed. Host cells containing an expression vector may be identified by any of a number of methods known in the art.

The protein desired to be expressed in the present invention comprises at least a lysine binding site of plasminogen. Types of lysine binding sites useful herein include rat, human, murine, and the like. The expression vectors and host cells of the invention may also be engineered to express other sequences which can result in expression of fusion proteins.

The DNA sequences of expression vectors, plasmids or DNA molecules of the present invention may be determined by various methods known in the art. For example, the dideoxy chain termination method as described in Sanger et al., Proc. Natl. Acad. Sci. USA 74, 5463–5467 (1977), or the Maxam-Gilbert method as described in Proc. Natl. Acad. Sci. USA 74, 560–564 (1977) may be employed.

It should, of course, be understood that not all expression vectors and DNA regulatory sequences will function equally well to express DNA sequences. Neither will all host cells function equally well with the same expression system. However, one of ordinary skill in the art may make a selection among expression vectors, DNA regulatory sequences, and host cells using the guidance provided herein without undue experimentation and without departing from the scope of the present invention.

Growth of the host cells may be achieved by one of ordinary skill in the art by the use of an appropriate medium. Appropriate media for growing host cells include those which provide nutrients necessary for the growth of the cells. A typical medium for growth includes necessary carbon sources, nitrogen sources, and trace elements. Inducers may also be added. The term "inducer", as used herein, includes any compound enhancing formation of the desired protein or peptide. Carbon sources may include sugars such as glucose, galactose, raffinose, and the like; organic acids such as sodium acetate, and the like; and alcohols such as ethanol. A preferred medium comprises Yeast Nitrogen Base (Difco) containing 2% glucose or 2% galactose and all necessary amino acids. The pH of the medium is preferably adjusted to about 5 to 6, more preferably about 5.

The present invention also concerns a process for producing the anti-angiogenic lysine binding fragments of the invention. The process comprises culturing the host cell of the invention in a suitable medium under conditions suitable for expression of the desired peptide. The process of the present invention is performed under conditions suitable for expression of the desired peptide. The pH of the medium is preferably maintained between 4.0 and 6.0, most preferably between 4.5 and 5.5, during the growth of host cells. A suitable temperature range for the process of the invention is from about 28° C. to about 32° C. Pressure is not known to be critical to practice of the invention and for convenience about atmospheric pressure is typically employed. The process of the invention is preferably carried out under aerobic conditions.

The peptide fragments of the invention are effective in treating diseases or processes that are mediated by, or involve, angiogenesis. The present invention includes the method of treating an angiogenesis mediated disease with an effective amount of the fragments of the invention. The angiogenesis mediated diseases include, but are not limited to, solid tumors, blood born tumors such as leukemias; tumor metastasis; benign tumors, for example, hemangiomas, acoustic acuromas, neurofibromas, trachomas, and pyogenic granulomas; rheumatoid arthritis;

psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; and wound granulation. The fragments are useful in treatment of disease of excessive or abnormal stimulation of endothelial cells. These diseases include, but are not limited to, intestinal adhesions, atherosclerosis, scleroderma, and hypertrophic scars, i.e., keloids. The fragments can be used as birth control agents by preventing vascularization required for embryo implantation.

The fragments may be used in combination with other compositions and procedures for the treatment of diseases. For example, a tumor may be treated conventionally with surgery, radiation or chemotherapy combined with the fragments and then angiostatin may be subsequently administered to the patient to extend the dormancy of micrometastases and to stabilize any residual primary tumor.

The protein fragments of the invention can be provided as isolated and substantially purified protein fragments and/or fusion proteins in pharmaceutically acceptable formulations using formulation methods known to those of ordinary skill in the art. These formulations can be administered by standard routes. In general, the combinations may be administered by the topical, transdermal, intraperitoneal, oral, rectal or parenteral (e.g., intravenous, subcutaneous or intramuscular) route. In addition, the active molecule(s) may be incorporated into biodegradable polymers allowing for sustained release of the compound, the polymers being implanted in the vicinity of where drug delivery is desired, for example, at the site of a tumor or implanted so that the active molecule is slowly released systemically. The biodegradable polymers and their use are described, for example, in detail in Brem et al., *J. Neurosurg.* 74:441–446 (1991), which is hereby incorporated by reference in its entirety.

The dosage of the peptide of the present invention will depend on the disease state or condition being treated and other clinical factors such as weight and condition of the human or animal and the route of administration of the compound. For treating humans or animals, between approximately 0.5 mg/kilogram to 500 mg/kilogram of the peptide can be administered. Depending upon the half-life of the peptide in the particular animal or human, the peptide can be administered between several times per day to once a week. It is to be understood that the present invention has application for both human and veterinary use. The methods of the present invention contemplate single as well as multiple administrations, given either simultaneously or over an extended period of time.

The peptide formulations include those suitable for oral, rectal, ophthalmic (including intravitreal or intracameral), nasal, topical (including buccal and sublingual), vaginal or parenteral (including subcutaneous, intraperitoneal, intramuscular, intravenous, intradermal, intratracheal, and epidural) administration. The peptide formulations may be conveniently presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiting only the addition of the sterile liquid carrier, for example, water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, the administered ingredient. It should be understood that in addition to the ingredients, particularly mentioned above, the formulations of the present invention may include other agents conventional in the art having regard to the type of formulation in question.

The following examples are further illustrative of the present invention. These examples are not intended to limit the scope of the present invention, and provide further understanding of the invention.

EXAMPLES

Experimental Procedures

Gene Construction, Expression, and Purification of Recombinant Human Angiostatin The human angiostatin fragment was amplified from a human plasminogen cDNA template (American Type Culture Collection, Rockville, Md.) by standard polymerase chain reaction (PCR) with the following two primers: 5'-GCGGATCCATGAAAGTGTATCTCTCAGAGTGCAAG (SEQ ID NO:7; forward primer for residue 98–458) and 5'-GCGGATCCTCACTATTCTGTTCCTGAGCA TTTTTTCAG (SEQ ID NO:8; reverse primer for residue 98–458). The amplified cDNA fragment was ligated into the BamHI site of the pMelBacA vector (InVitrogen, San Diego, Calif.). The pMelBac A vector containing angiostatin cDNA was then co-transfected into Sf9 cells with viral BaculoGold™ DNA (PharMingen, San Diego, Calif.). Briefly, $1\times10^6$ Sf9 cells were seeded in a T25 tissue culture flask and incubated at 27° C. with 1 ml of the transfection solution containing 2 mg of transfer vector DNA, 0.5 mg of BaculoGold™ DNA, and 6 ml of Cellfectin (Gibco BRL, Gaithersburg, Md.). The transfection solution was removed 4 hours post-transfection and replaced with 3 ml of Sf900II medium (Gibco BRL, Gaithersburg, Md.). Four days after incubation, the viral supernatant was harvested and individual clones were identified by limiting dilution. The clone with the highest protein expression, as determined by SDS-PAGE/Coomassie blue staining, was amplified in Sf9 cells for protein production. High Five insect cells (InVitrogen, San Diego, Calif.) ($1.5\times10^6$ cells/ml) were infected with approximately $1\times10^7$ viral particles/ml of the recombinant virus. After 48 hours, the culture supernatant was collected by centrifugation at 5,000×g for 30 minutes. The supernatant was then applied to a lysine sepharose column and angiostatin protein eluted with e-aminocapronic acid as previously described. To block the lysine-binding sites, angiostatin was then incubated at 1:2 molar ratio with trans-aminomethylcyclohexanecarboxylic acid (AMCHA) at room temperature for 30 minutes. The angiostatin-AMCHA complex was then dialyzed twice against 500 volumes of DMEM (Gibco BRL, Gaithersburg, Md.) at 4° C.

Gene Construction, Expression, and Purification of Kringle Fragments of Angiostatin The cDNA fragments encoding K1, K2, K3, K4, K1-3, and K2-3 were amplified from human plasminogen cDNA template (American Type Culture Collection, 10801 University Boulevard, Manassas, Va. 20110) by standard polymerase chain reaction (PCR).

PCR fragments of K2, K3, and K2-3 were cloned into pQE8 vector and recombinant proteins expressed in bacterial strain M15 (K3 and K2-3) and BL21 (K2) as previously described. The cysteine residue 169 of K2 and 297 of K3 were mutated to serines in order to eliminate interkringle disulfide bridge formation. Recombinant kringle 2-3 also contains a hexahistidine tag for purification. Recombinant K2, K3, and K2-3 were purified to homogeneity as described. The recombinant K1 and K4 were expressed in Pichia Pastoris system and purified to homogeneity as described elsewhere. K1-3 fragment was produced as previously reported. For the production of K1 and K4 fragment, the plasmid constructs, pPIC9K[$K1_{HPg}$-$K5_{HPg}$] and pPIC9K [$K4_{HPg}$-$K5_{HPg}$], were linearized with restriction endonuclease Sac I and used for transformation of the GS-115 and KM 71 strain of Pichiapastorzs by electroporation, respectively. Selection procedures for isolation of appropriate clones and protocols for high bio-mass fermentation were performed as described in other works. The fermentation medium was passed over a lysine-Sepharose column as previously described. The $K1_{HPg}$-$K5_{HPg}$ protein was extensively dialyzed against water, lyophilized, and subsequently digested with Factor Xa (Fxa) (Enzyme Research Labs. South Bend, Ind.) for 6 hours at room temperature in 0.05 M Tris/5 mM $CaCl_2$ (pH 7.4) using a protein: FXa ratio of 1:50 (w/w). The $K4_{HPg}$-$K5_{HPg}$ protein was digested with elastase for 16 hours at room temperature in 0.1 M phosphate/15 mM e-aminocapronic acid (E-ACA) (pH 7.8) using a protein: elastase ratio of 1:250 (w/w). The digests were dialyzed against water to remove the E-ACA and then reapplied to a lysine-Sepharose column. The recombinant proteins were batch eluted from the column using 20 mM E-ACA, extensively dialyzed against water, and then lyophilized.

Endothelial Cell Migration Assay

Bovine capillary endothelial (BCE) cells were harvested from bovine adrenal glands as previously described (33). BCE cells were maintained in DMEM in the presence of 10% bovine calf serum, 1% antibiotics, and 3 ng/ml of bFGF (PeproTech, Rockhill, N.J.). To evaluate endothelial cell migration, a Boyden Chamber-based assay was performed. First, the polycarbonate membranes with 8 mm pore sizes (Neuro Probe Inc., Cabin John, Md.) were coated with 100 mg/ml of collagen type I following manufacturer's instructions (Becton Dickinson, Bedford, Mass.). BCE cells between passage 10 to 14 were harvested with 0.05% trypsin solution, washed, resuspended to a density of 75,000 cells/ml in DMEM containing 10% bovine calf serum and 10 ng/ml of bFGF, and incubated at 37° C. for 30 minutes. During cell incubation, various concentrations of kringle fragments were loaded into the lower chambers. The collagen-coated membrane filter was placed on top of the lower chamber and the top chamber then attached. After the 30 minute incubation, BCE cells were loaded into the top chamber and incubated at 37° C. for 4 hours. The chemotaxis chamber was then dismantled and the filter membrane removed. The non-migrated cells were scraped off the upper surface of the membrane with cotton swabs three times. After rinsing with PBS, the membrane was fixed with 10% buffered formalin for 45 minutes and then stained with Gill No. 2 hematoxylin overnight (J. B. Baker, Phillipsburg, N.J.). The membrane was then rinsed with PBS and mounted with Cytoseal (Stephens Scientific, Riverdale, N.J.). Each sample was tested in quadruplicate and a representative field in each well was counted at 10 x magnification to determine the number of migrated cells.

Reduction and Alkylation of Angiostatin

Fifty micrograms of the recombinant angiostatin in 300 ml of serum-free DMEM was reduced by incubating with 15 ml of 0.5 M dithiothreitol for 15 minutes at the room temperature. The reduced angiostatin protein was then alkylated with 30 ml of 0.5 M iodoacetamide. The reaction mixture was dialyzed against 500 volumes of DMEM at 4° C. overnight and further dialyzed against another 500 volumes of fresh DMEM for an additional 4 hours. The homogeneity of the reduced and alkylated angiostatin was analyzed by SDS-PAGE before being examined for its inhibition on BCE cell migration. The endotoxin concentrations of both native and reduced/alkylated angiostatin were evaluated according to manufacturer's instructions (Associates of Cape Cod, Woods Hole, Mass.).

Results

Characterization of Recombinant Kringle Domains of Human Plasminogen (HPg)

HPg is a circulating zymogen of plasmin, a serine protease that plays a pivotal role in fibrinolysis. HPg is present in circulation as a single-chain glycoprotein of 791 amino acids. It contains a signal leader sequence, a pre-activation peptide, 5 triple-disulfide bridged kringle domains, and a protease domain. Angiostatin is an internal fragment of HPg and spans from K1 to K4. The four kringles of angiostatin are highly homologous. Each kringle has about 80 amino acids and consists of three pairs of disulfide bonds with two lysine-binding sites on K1 and K4, and at least one on K2. To determine the anti-endothelial cell activities of individual kringles, recombinant angiostatin (K1-4), K1-3, K2-3, K1, K2, K3, and K4 were produced as described (See Experimental Procedures). These kringle variants were characterized on SDS-PAGE and stained with Coomassie blue. The recombinant angiostatin migrated with a greater molecular size of approximately 65 kD, which may be attributed to the heavy glycosylation of the Bacculovirus recombinant protein. K1-3 and K2-3 migrated with predicted molecular sizes of 38 kD and 25 kD, respectively. Each individual kringle displayed predicted molecular sizes of 10 kD with the only exception of K1, which manifested a higher molecular size of 17 kD due to oligomerization.

Inhibition of Endothelial Cell Migration by Angiostatin and Complementary Anti-endothelial Cell Activities of K1-3 and K4 of Hpg Basic FGF (10 ng/ml) was used to stimulate the migration of BCE cells. Angiostatin inhibited the bFGF-induced BCE cell migration in a dose-dependent manner with an IC50 of approximately 50 nM. Surprisingly, K1-3 only displayed a marginal anti-migratory effect whereas K4, despite being an individual kringle, exhibited potent inhibitory activity with an IC50 of 500 nM. It was previously described that K1-3 is a potent antagonist for endothelial cell proliferation. However, our data demonstrate that it is only a modest inhibitor of endothelial cell migration. In contrast, K4 was reported to have a negligible effect on endothelial cell proliferation and yet, we now show it is an effective anti-migratory agent. As K1-3 and K4 are structurally combined, the resulting angiostatin, or K1-4, becomes an effective inhibitor of both endothelial cell proliferation and migration, suggesting that K1-3 and K4 are both required for the potent inhibitory functions of angiostatin with their complementary anti-endothelial cell activities.

Inhibition of Endothelial Cell Migration with K1-3, K2-3, K1, K2, and K3

To determine the structural components that are responsible for the anti-migratory functions of angiostatin, we further examined the inhibitory activities of smaller kringle fragments. K1-3 is thus fragmented into K1 and K2-3. As opposed to K1-3, K2-3 displayed a marked increase in the anti-migratory effect with an IC50 of approximately 100 nM whereas K1 was only a modest inhibitor, indicating that the functional elements for the inhibition of migration may reside on K2-3. After K2-3 is further segmented into K2 and K3, both fragments manifest comparable dose-dependent anti-migratory activities relative to K2-3, implying that the anti-migratory motifs may be shared by both K2 and K3.

Interactions among Kringle Fragments Alter Their Anti-migratory Activities

To elucidate the interactions among different kringles, we assessed various kringle combinations on bFGF-elicited endothelial cell migration. As compared with the potent inhibitory effect of angiostatin, K4 had a similar activity whereas K1-3 was remarkably less active. However, a combination of K1-3 and K4 resulted in an anti-migratory activity comparable to angiostatin, indicating that angiostatin entails the additive contributions of K1-3 and K4 for its potent anti-endothelial cell function. On the contrary, a combination of K1 and K2-3 failed to show any additive effect as compared with K2-3 alone, which could result from two alternative mechanisms. First, the inhibitory activity of K2-3 on endothelial cells was already saturated so that K1 could not produce any additional anti-migratory effect. Second, K1 is too modest an antagonist to potentiate the inhibitory function of K2-3. Moreover, K2-3 had a similar anti-migratory effect as opposed to its smaller fragments, K2 or K3, or the combination of K2 and K3. It is conceivable that both K2 and K3 may have the functional motifs for anti-migratory effects and the interkringle interactions between K2 and K3 may alter their functions so that no additive effects could result from a combination of K2 and K3.

Kringle Structures and Lysine-binding Sites are Essential for the Potent Anti-migratory Function of Angiostatin Because angiostatin is composed of 4 triple-disulfide bridged kringle domains with 2–3 or more lysine binding sites, it is of interest to determine the roles of these structures in suppressing endothelial cell migration. Angiostatin was thus reduced to disrupt the kringle conformation and the reduced product was alkylated to prevent refolding. Relative to native product, the reduced angiostatin had a markedly decreased anti-migratory efficacy. Furthermore, AMCHA, a high affinity lysine analogue, was used to block the lysine-binding sites of angiostatin. Surprisingly, blocking the lysine-binding sites abolished the anti-migratory function of angiostatin. Taken together, these data led to the conclusion that both kringle structures and lysine-binding sites may play crucial roles in the functions of angiostatin.

What is claimed is:

1. A polypeptide having less than 70 amino acids and comprising the amino acid sequence set forth in SEQ ID NO: 4, wherein said polypeptide comprises a fragment of kringle 1 of human plasminogen containing a lysine binding site and having anti-angiogenic activity.

2. A polypeptide consisting of SEQ ID NO:4, wherein said polypeptide comprises a fragment of kringle 1 of human plasminogen containing a lysine binding site and having anti-angiogenic activity.

* * * * *

SEQUENCE LISTING

```
<160> NUMBER OF SEQ ID NOS:  8

<210> SEQ ID NO 1
<211> LENGTH: 82
<212> TYPE: PRT
<213> ORGANISM: human

<400> SEQUENCE: 1

Ser Glu Cys Lys Thr Gly Asn Gly Lys Asn Tyr Arg Gly Thr Met Ser
  1               5                  10                  15

Lys Thr Lys Asn Gly Ile Thr Cys Gln Lys Trp Ser Ser Thr Ser Pro
             20                  25                  30

His Arg Pro Arg Phe Ser Pro Ala Thr His Pro Ser Glu Gly Leu Glu
         35                  40                  45

Glu Asn Tyr Cys Arg Asn Pro Asp Asn Asp Pro Gln Gly Pro Trp Cys
     50                  55                  60

Tyr Thr Thr Asp Pro Glu Lys Arg Tyr Asp Tyr Cys Asp Ile Leu Glu
 65                  70                  75                  80

Cys Glu

<210> SEQ ID NO 2
<211> LENGTH: 84
<212> TYPE: PRT
<213> ORGANISM: human
```

```
<400> SEQUENCE: 2

Val Gln Asp Cys Tyr His Gly Asp Gly Gln Ser Tyr Arg Gly Thr Ser
  1               5                  10                  15

Ser Thr Thr Thr Thr Gly Lys Lys Cys Gln Ser Trp Ser Ser Met Thr
             20                  25                  30

Pro His Arg His Gln Lys Thr Pro Glu Asn Tyr Pro Asn Ala Gly Leu
             35                  40                  45

Thr Met Asn Tyr Cys Arg Asn Pro Asp Ala Asp Lys Gly Pro Trp Cys
         50                  55                  60

Phe Thr Thr Asp Pro Ser Val Arg Trp Glu Tyr Cys Asn Leu Lys Lys
 65                  70                  75                  80

Cys Ser Gly Thr

<210> SEQ ID NO 3
<211> LENGTH: 78
<212> TYPE: PRT
<213> ORGANISM: human

<400> SEQUENCE: 3

Cys Met His Cys Ser Gly Glu Asn Tyr Asp Gly Lys Ile Ser Lys Thr
  1               5                  10                  15

Met Ser Gly Leu Glu Cys Gln Ala Trp Asp Ser Gln Ser Pro His Ala
             20                  25                  30

His Gly Tyr Ile Pro Ser Lys Phe Pro Asn Lys Asn Leu Lys Lys Asn
             35                  40                  45

Tyr Cys Arg Asn Pro Asp Arg Glu Leu Arg Pro Trp Cys Phe Thr Thr
         50                  55                  60

Asp Pro Asn Lys Arg Trp Glu Leu Cys Asp Ile Pro Arg Cys
 65                  70                  75

<210> SEQ ID NO 4
<211> LENGTH: 38
<212> TYPE: PRT
<213> ORGANISM: human

<400> SEQUENCE: 4

Arg Phe Ser Pro Ala Thr His Pro Ser Glu Gly Leu Glu Glu Asn Tyr
  1               5                  10                  15

Cys Arg Asn Pro Asp Asn Asp Pro Gln Gly Pro Trp Cys Tyr Thr Thr
             20                  25                  30

Asp Pro Glu Lys Arg Tyr
             35

<210> SEQ ID NO 5
<211> LENGTH: 17
<212> TYPE: PRT
<213> ORGANISM: human

<400> SEQUENCE: 5

Asp Lys Gly Pro Trp Cys Phe Thr Thr Asp Pro Ser Val Arg Trp Glu
  1               5                  10                  15

Tyr

<210> SEQ ID NO 6
<211> LENGTH: 46
<212> TYPE: PRT
<213> ORGANISM: human

<400> SEQUENCE: 6
```

```
Trp Asp Ser Gln Ser Pro His Ala His Gly Tyr Ile Pro Ser Lys Phe
 1               5                  10                 15

Pro Asn Lys Asn Leu Lys Lys Asn Tyr Cys Arg Asn Pro Asp Arg Glu
             20                  25                 30

Leu Arg Pro Trp Cys Phe Thr Thr Asp Pro Asn Lys Arg Trp
         35                  40                  45

<210> SEQ ID NO 7
<211> LENGTH: 35
<212> TYPE: DNA
<213> ORGANISM: human

<400> SEQUENCE: 7
gcggatccat gaaagtgtat ctctcagagt gcaag                      35

<210> SEQ ID NO 8
<211> LENGTH: 38
<212> TYPE: DNA
<213> ORGANISM: human

<400> SEQUENCE: 8
gcggatcctc actattctgt tcctgagcat tttttcag                   38
```